(12) United States Patent
Wang et al.

(10) Patent No.: US 9,187,520 B2
(45) Date of Patent: Nov. 17, 2015

(54) METHOD FOR PREPARING INSULIN GLARGINE CRYSTAL

(75) Inventors: Damei Wang, Beijing (CN); Wenjie Li, Beijing (CN); Jinlei Zhang, Beijing (CN)

(73) Assignee: Gan & Lee Pharmaceuticals, Tongzhou District, Beijing (CN)

( * ) Notice: Subject to any disclaimer, the term of this patent is extended or adjusted under 35 U.S.C. 154(b) by 53 days.

(21) Appl. No.: 14/116,556

(22) PCT Filed: Apr. 19, 2012

(86) PCT No.: PCT/CN2012/074392
§ 371 (c)(1),
(2), (4) Date: Dec. 18, 2013

(87) PCT Pub. No.: WO2012/152175
PCT Pub. Date: Nov. 15, 2012

(65) Prior Publication Data
US 2014/0155574 A1  Jun. 5, 2014

(30) Foreign Application Priority Data
May 9, 2011  (CN) .......................... 2011 1 0118026

(51) Int. Cl.
*C07K 14/62* (2006.01)
*C07K 1/30* (2006.01)
*C30B 7/14* (2006.01)
*C30B 29/58* (2006.01)

(52) U.S. Cl.
CPC ................. *C07K 1/306* (2013.01); *C07K 14/62* (2013.01); *C30B 7/14* (2013.01); *C30B 29/58* (2013.01)

(58) Field of Classification Search
CPC .............................. C07K 14/62; A61K 38/28
See application file for complete search history.

(56) References Cited

U.S. PATENT DOCUMENTS

| 2,143,590 | A | * | 1/1939 | Scott .............................. 530/303 |
| 2,920,104 | A | | 1/1960 | Brooks et al. |
| 3,719,655 | A | * | 3/1973 | Jackson ........................ 530/305 |
| 4,959,351 | A | * | 9/1990 | Grau .............................. 514/6.2 |
| 5,504,188 | A | * | 4/1996 | Baker et al. ................... 530/304 |
| 5,656,722 | A | | 8/1997 | Dorschug |
| 7,803,763 | B2 | | 9/2010 | Thurow et al. |
| 2011/0236925 | A1 | * | 9/2011 | Hazra et al. ................... 435/68.1 |

FOREIGN PATENT DOCUMENTS

| CN | 88102311 | 2/1996 |
| CN | 1128271 A | 1/2005 |
| CN | 95106555.6 | 1/2005 |
| CN | 102219851 | 5/2012 |
| CN | 101035557 A | 9/2012 |

OTHER PUBLICATIONS

Berchtold et al. "Binding of Phenol to R6 Insulin Hexamers," Biopolymers (Peptide Science), vol. 51, 165-172 (1999).*
Barnett "Basal insulin—answers from analogues" Practical Diabetes Int 2002; 19(7): 213-216.*
Markussen et al. "Soluble, prolonged-acting insulin derivatives. I. Degree of protraction and crystallizability of insulins substituted in the termini of the B-chain" Protein Engineering, vol. 1, 205-213 (1987).*
Abel J. J, PNAS, 12:132(1926).
J. Stewart, et al, Solid Phase Peptide Synthesis, Freeman and Co., San Francisco, 1969.

* cited by examiner

*Primary Examiner* — Christina Bradley
(74) *Attorney, Agent, or Firm* — Stites & Harbison PLLC; Cong Ding

(57) ABSTRACT

Disclosed is a method for preparing an insulin glargine ($Gly^{A21}$-$Arg^{B31}$-$Ary^{B32}$-human insulin) crystal, comprising crystallizing the insulin glargine at pH 7.0-9.0 and in a crystallization solution containing a recombinant insulin glargine, an organic solvent of a 10-30% concentration by volume, a zinc compound, a phenol derivative, a salt and an organic acid.

13 Claims, 6 Drawing Sheets

METHOD FOR PREPARING INSULIN GLARGINE CRYSTAL

CROSS REFERENCE TO RELATED APPLICATIONS

This application is a §371 National State Application of PCT/CN2012/074392 filed Apr. 19, 2012 which claims priority to CN 201110118026.2 filed May 9, 2011.

TECHNICAL FIELD

The present invention relates to a method for preparing human insulin analogue crystal, particularly relates to a method for preparing recombinant insulin glargine (recombinant $Gly^{A21}$-$Arg^{B31}$-$Arg^{B32}$-human insulin) crystal.

BACKGROUND ART

Diabetes is a common endocrine and metabolic disease. In recent years, the morbidity of diabetes in the world has been increasing rapidly. With the change of people's life style and quick population aging process in China, the morbidity of diabetes tends to rise rapidly. In 2010, the total number of diabetics in China has been more than 90 million. Diabetes which has become another major noninfectious chronic disease subsequent to cardio-cerebrovascular disease and tumor, severely impairs the health of people. The acute or chronic complications of diabetes, in particular, chronic complications, affect several organs; they have high morbidity and mortality, seriously affect the patient's physical and mental health, and thus bring a heavy burden to individual, family and society.

Insulin therapy is always considered as an important means for treating diabetes and controlling blood sugar suitably. Recently, with the development of the insulin techniques, a new generation of insulin with different acting-time, i.e. insulin analogs, are developed, wherein a newly developed long-acting insulin analog, i.e. insulin glargine, is being accepted and used by more and more physicians and patients.

Recombinant insulin glargine (or recombinant $Gly^{A21}$-$Arg^{B31}$-$Arg^{B32}$-human insulin, or recombinant $Gly^{A21}$-human insulin-$Arg^{B31}$-$Arg^{B31}$-OH) is obtained by mutating asparagine (Asn) at A21 in chain A of human insulin into glycine (Gly), and adding two arginines (Arg) to the carboxyl terminal of chain B (see: U.S. Pat. No. 5,656,722). The recombinant insulin glargine is able to simulate physiological basis insulin secretion (steady and no peaks), when using it to control the blood sugar to reach the standard level, the patient almost has no risk of low blood sugar, and the pharmaceutical effect can last about 24 hours, which is consistent with work-rest cycle of human life. As a result, it only needs to be injected once per day and is favored by patients and doctors.

In existing recombinant insulin glargine products, most of the recombinant insulin glargines are in the form of solution or amorphous dry powder, without forming crystal. However, the crystal form of recombinant insulin glargine is a better form for application, since it has uniform and steady solid molecular form and small sediment volume, and is easy to be separated from the supernatant, the time for centrifugation and freeze-drying is short, and the production efficiency is relatively high. It is thus desirable to prepare recombinant insulin glargine crystals and then apply the crystals to insulin pharmaceutical preparations.

There are many methods for crystallizing insulin in the prior art, for example, those described in Abel J. J, PNAS, 12: 132(1926), U.S. Pat. No. 2,920,104, CN 95106555.6, etc. However, after extensive research on all kinds of crystallization processes of insulins and analogues thereof, the inventors have found out that the prior methods for crystallizing insulin cannot make the recombinant insulin glargine form crystals: 1) under the conditions for crystallizing human insulin: 0.25M acetic acid, 1.6-2.1 g/L human insulin, 2% zinc, pH 5.95-6.05, insulin glargine cannot form hexahedron crystals, and only exists in the form of amorphous precipitate; 2) under the conditions for crystallizing recombinant Lys-Pro-insulin ($Lys^{B28}$-$Pro^{B29}$-human insulin): 1M acetic acid, 1.8-2.5 g/recombinant Lys-Pro-insulin, 100-300 mg of zinc, 0.2% phenol, pH 5.9-6.2, insulin glargine still cannot form hexahedron crystals, and only exists in the form of amorphous precipitate.

The reason why the prior methods for crystallizing insulin cannot make the recombinant insulin glargine form crystals may lie in that: recombinant insulin glargine has two additional basic amino acids ($Arg^{B31}$-$Arg^{B32}$) at the terminal of chain B, which cause its isoelectric point higher than that of natural human insulin, so that under prior conditions for crystallizing insulin, the recombinant insulin glargine can only exist in amorphous state, and cannot form steady hexahedron crystals.

SUMMARY OF THE INVENTION

The object of the invention is to solve the above problems and provide a method for preparing recombinant insulin glargine crystal, the method can prepare insulin glargine-zinc crystal with high quality and high yield in large scale. The crystal has steady solid molecular form, may be readily prepared in large scale, and has small sediment volume so that separation of it from supernatant is easy. Furthermore, the time for centrifugation and freeze-drying of the crystal is short and the production efficiency of the crystal is high.

Accordingly, in order to achieve the object of the invention, the present invention provides a method for preparing recombinant insulin glargine crystal, the method comprises the steps of crystallizing the recombinant insulin glargine at pH 7.0-9.0 and in a crystallization solution containing a recombinant insulin glargine, an organic solvent, a zinc compound, a phenol derivative, a salt and an organic acid, wherein the concentration of volume percent of the organic solvent is 10-30%.

It is difficult to crystallize recombinant insulin glargine, because its isoelectric point is significantly different from those of other insulins, the addition of organic solvent and adjustment of pH during the crystallization process are thus key factors to affect crystallization results.

The organic solvent according to the present invention is one of the key factors for recombinant insulin glargine to form crystal. Other insulins can form crystal in the absence of organic solvent, while recombinant insulin glargine only forms amorphous precipitate instead of crystal in the absence of organic solvent. Through extensive experimental research, the inventors find out that, the recombinant insulin glargine begins to form crystal only in the presence of an organic solvent at a concentration of volume percent of 10-30% in the crystallization solution, which is possibly due to the fact that organic solvent in the crystallization solution can reduce the solubility of recombinant insulin glargine: (1) when organic solvent is present in the crystallization solution, it can reduce electrolytic constant of the crystallization solution, and increase the mutual attraction force between different electric charges on the insulin glargine molecules, thereby leading to a decrease of the solubility of insulin glargine; (2) the interaction between the organic solvent and water can destroy the hydrated shells of insulin glargine, and also reduce the solubility of insulin glargine.

Since the organic solvent may reduce the solubility of recombinant insulin glargine in the crystallization solution, thereby facilitating the formation of insulin glargine crystal, the concentration of volume percent of organic solvent in the crystallization solution is thus preferably not less than 10% (vol./vol.). Otherwise, it is difficult to achieve the above effects. Meanwhile, if the concentration of the organic solvent is too high, it tends to cause protein denaturation and inactivation. Thus the concentration of volume percent of organic solvent in the crystallization solution is preferably not more than 30% (vol./vol.). According to the present invention, the organic solvent may be any organic solvents which are apt to dissolve in water and well-known to a person skilled in the art, including acetonitrile, ethanol, n-propanol, isopropanol and the like. Preferably the organic solvent is ethanol.

Additionally, since the recombinant insulin glargine has a relatively high isoelectric point between pH 6-8, while other insulins generally have the isoelectric points between pH 5-5.5, the recombinant insulin glargine only becomes slightly turbid at the crystallization pH value (e.g. pH 6) of other insulins, and such a pH value is not enough to initiate the crystallization process, only when the pH is higher than 7, the crystallization process starts. Hence, the condition of crystallization according to the present invention is pH 7.0-9.0, while at such pH, other insulins are substantively clear and cannot form crystals. Moreover, the inventors find out through the study that more regular and uniform crystals with bigger particle size can be formed if the pH value of the initial crystallization solution is adjusted to pH 8.0-9.0, and during the crystallization process of recombinant insulin glargine, pH value of the crystallization solution is adjusted to pH 7.0-8.0. The pH value of the crystallization solution according to the present invention can be adjusted by any methods which are well-known to the person skilled in the art, including using alkali, preferably using sodium hydroxide, potassium hydroxide, ammonium hydroxide (strong ammonia).

Preferably, the concentration of the recombinant insulin glargine in the crystallization solution is 2-4 g/L, more preferably 2.8-3.2 g/L. If the concentration of the insulin glargine is too low, it will increase the volume of the crystallization solution, which is disadvantageous to large scale production; if the concentration is too high and higher than the solubility of insulin glargine, it will make the solution turbid.

Preferably, the zinc compound is added in the form of zinc salts selected from those which can dissociate into zinc ions in water, representative examples of zinc salts includes zinc chloride, zinc oxide, zinc acetate, zinc bromide and zinc sulfate. A person skilled in the art will understand that many other zinc salts may also be used in the method according to the present invention. The concentration of zinc in the crystallization solution of the present invention is preferably 20-200 mg/L. More preferably the zinc of the present invention is zinc chloride, and its concentration is 70-100 mg/L. Since zinc compound is involved in the insulin glargine crystallization process, if the concentration of the zinc compound is too low, it will make the crystallization of insulin glargine incomplete; and if the concentration of the zinc compound is too high, it will increase the number of the crystal nucleus in the initial crystallization stage, and thereby make the size of crystal smaller.

Preferably, the phenol derivative refers to substance which can provide phenolic hydroxyl, and are selected from phenol, m-cresol and methyl p-hydroxybenzoate, or a mixture thereof; the concentration of the phenol derivative in the crystallization solution is 0.05-0.5 g/100 ml (i.e. 0.05-0.5%, wt./vol.). More preferable phenol derivative is phenol, and its concentration is 0.1-0.2 g/100 ml (i.e. 0.1-0.2%, wt./vol.). The phenol derivative is also involved in the crystallization process of insulin glargine. If the concentration of phenol derivative is too low, it is disadvantageous to crystal formation; and if the concentration of phenol derivative is too high, it will not influence the crystallization process, but will increase the production cost.

Preferably, the salt refers to strong electrolyte salt which is soluble in water and is selected from sodium chloride, sodium acetate or sodium citrate; the concentration of the salt in crystallization solution is 0.1-0.5M. Preferably, the salt is sodium chloride and its concentration is 0.3-0.4M. If the concentration of the salt is lower than 0.1M, the crystallization solution is turbid at pH 7.0-9.0, and cannot effectively form crystal; if the concentration of the salt is higher than 0.5M, the crystallization solution will always be clear liquid at pH 7.0-9.0 and cannot form crystal either.

Preferably, the organic acid refers to short chain carboxylic acid apt to dissolve in water, and is selected from acetic acid, citric acid or glycine. If the concentration of organic acid is too high during the crystallization process, it will cause too much heat release in the crystallization process, thereby influencing the stability of the product; if the concentration of organic acid is too low, it will cause poor dissolution for the recombinant insulin glargine. Accordingly, the concentration of organic acid in the crystallization solution is preferably 0.3-0.8M. More preferably, the organic acid is acetic acid, and its concentration is 0.4-0.6M.

The temperature of crystallization is not crucial, the acceptable temperature range is about 1-30° C. The temperature of the initial crystallization solution is preferably at room temperature (10-30° C.), such a temperature can increase the solubility of the recombinant insulin glargine before crystallizing; the temperature during the crystallization process is preferably in the range of 2-8° C., such a low temperature can facilitate reducing the solubility of the recombinant insulin glargine, thereby accelerating the crystallization speed.

According to the present invention, preferably, the crystallization of recombinant insulin glargine is conducted by using the following steps: (1) preparing a crystallization solution comprising the above components with the above-mentioned contents, and adjusting the pH value of the initial crystallization solution to 8.0-8.5; (2) lowering the temperature of the above crystallization solution to 2-8° C., adjusting the pH value to 7.1-7.8, and then crystallizing for at least 3 hours.

The manner of dissolving recombinant insulin glargine into the crystallization solution and the order of adding each component to the crystallization solution are not crucial for the present invention. For example, the organic solvent, the zinc, the phenol derivative, the organic acid and the salt may be added into the solution of recombinant insulin glargine respectively. Alternatively, the zinc, the phenol derivative, the organic acid and the salt may be firstly prepared into solution, and then added to a solution comprising the recombinant insulin glargine and the organic solvent.

In the industrial production process, a re-crystallization process may be selected in order to make the insulin crystal more pure, the method of washing the crystal with water may also be used to reduce the amount of other solvents in the crystal.

The recombinant insulin glargine of the present invention can be available commercially, and also can be prepared by using any well-known peptide synthesis technique, such as solution method, solid phase synthesis (J. Stewart et al, "Solid Phase Peptide Synthesis", Freeman and Co., San Francisco, 1969), semi-synthesis, gene engineering technique, DNA recombinant (U.S. Pat. No. 5,656,722), etc.

The method for preparing recombinant insulin glargine crystal according to the present invention has the following advantages: recombinant insulin glargine hexahedron crystals with uniform and steady form can be obtained, the crystals have high transparency and small sediment volume; and the time for centrifugation and drying is short, the production efficiency is relatively high.

DETAILED DESCRIPTION OF THE INVENTION

Materials

Insulin glargine is from GAN & LEE Pharmaceuticals, Batch Number: GLGB09001.

Zinc chloride is commercially available from Beijing Andiyongfu Co., Ltd. , Batch Number: 71770; phenol is commercially available from Hengjian Pharmaceuticals in hangmen, Batch Number: 081001; acetic acid is commercially available from Xinning Pharmaceuticals in Taishan, Batch Number: 20081007; sodium chloride is commercially available from Yanjing Pharmaceuticals in Beijing, Batch Number: 080522; strong ammonia is commercially available from Beijing Huateng Hi-tech Corp., Batch Number: 20080513; ethanol is commercially available from Tianjin Kemiou Chemical Reagent Co., Ltd., Batch Number: 091005; ammonium acetate is commercially available from Shanghai Ketong Chemical Co., Ltd., Batch Number: 20081101; acetonitrile is commercially available from Shanghai Xingke Biochemistry Co., Ltd., Batch Number: 20091005; sodium acetate is commercially available from Tianjin Kemiou Chemical Reagent Co., Ltd., Batch Number: 090504.

EXAMPLE 1

Recombinant insulin glargine crystallization solution is prepared, in which the components and the concentrations thereof are as follows: recombinant insulin glargine: 3.5 g/L; acetonitrile: 20%; acetic acid: 0.7M; phenol: 0.4%; zinc chloride: 120 mg/L; sodium acetate: 0.5M.

6.3 g of recombinant insulin glargine is dissolved in 1L of pure water to form a suspension of the recombinant insulin glargine; additionally, 360 ml of acetonitrile, 72.09 ml of glacial acetic acid, 72 ml of 10% phenol solution, 4.25 ml of 5.08 g/100 ml (i.e. 5.08%, wt./vol.) zinc chloride solution, 225 ml of 4M sodium acetate solution are mixed together, and water is add thereto to a final volume of 0.6L. The above 0.6L of solution is added to the above 1L of recombinant insulin glargine suspension, and water is added thereto to a final volume of 1.8L, thereby forming a crystallization solution.

The initial temperature of the above crystallization solution is adjusted to 20-25° C., and the pH value is adjusted to pH 7.8-8.2 with ammonium hydroxide, the solution is stirred for 10 min until the solution is slightly turbid, the solution stands for crystallization at 2-8° C., for 3 hours. Then the supernatant is taken for HPLC detection, the content of recombinant insulin glargine in the supernatant is 0.05 mg/ml and meets the requirements.

Figure 1:
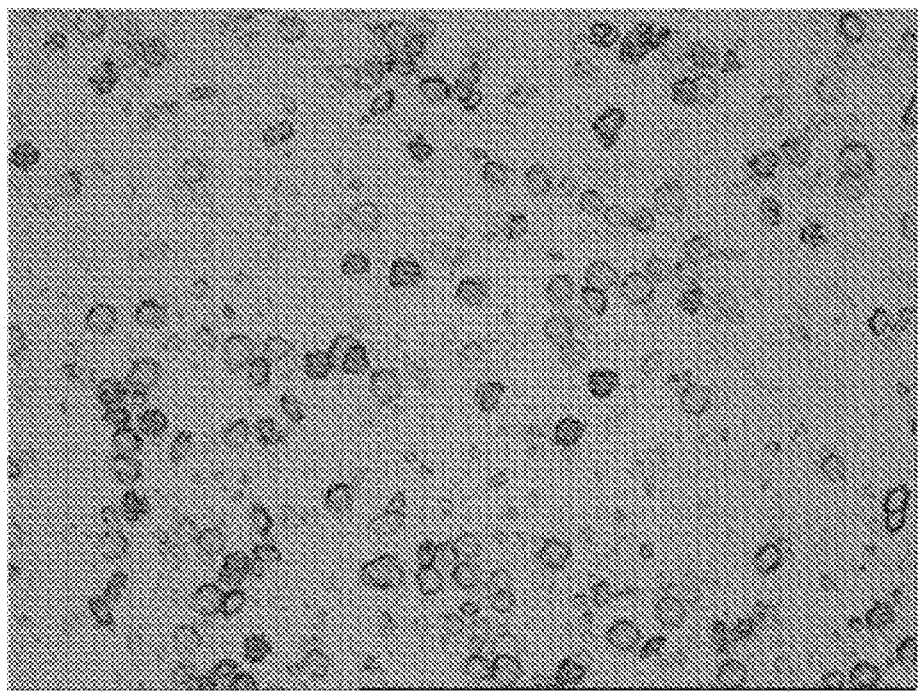
FIG. 1 is a microscopic view photograph at magnification of 160, showing the crystals of recombinant insulin glargine from Example 1.

By microscopic examination after stirring the crystallizing suspension, hexahedron crystals can be seen at magnification of 160, and the transparency is high (see: FIG. 1).

EXAMPLE 2

Recombinant insulin glargine crystallization solution is prepared, in which the components and the concentrations thereof are as follows: recombinant insulin glargine: 3 g/L; ethanol: 15%; acetic acid: 0.5M; zinc chloride: 90 mg/L; phenol: 0.2%; sodium chloride: 0.3M.

251.8 g of recombinant insulin glargine is added to a clean stainless container, 13.1 L of 96% ethanol, 2.4 L of pure glacial acetic acid, 148.6 ml of 5.08 g/100 ml (i.e. 5.08%, wt./vol.) zinc chloride solution, 1678 ml of 10% phenol solution, and 1472 g of sodium chloride are added thereto, and then water is added thereto to a final volume of 83.9 L.

The initial temperature of the above crystallization solution is adjusted to 23±2° C., and the pH value thereof is adjusted to pH 8.0-8.5 with strong ammonia, the solution is stirred for 10 min until the solution is slightly turbid, the solution stands at 2-8° C. to cool for 1 hour, and then the pH value is adjusted to pH 7.1-7.6 with glacial acetic acid. Then the solution is stirred for 10 min and stands at 2-8° C. for 10 hours. Then the supernatant is taken for HPLC detection, the content of recombinant insulin glargine in the supernatant is as low as 0.02 mg/ml and meets the requirements.

Figure 2:
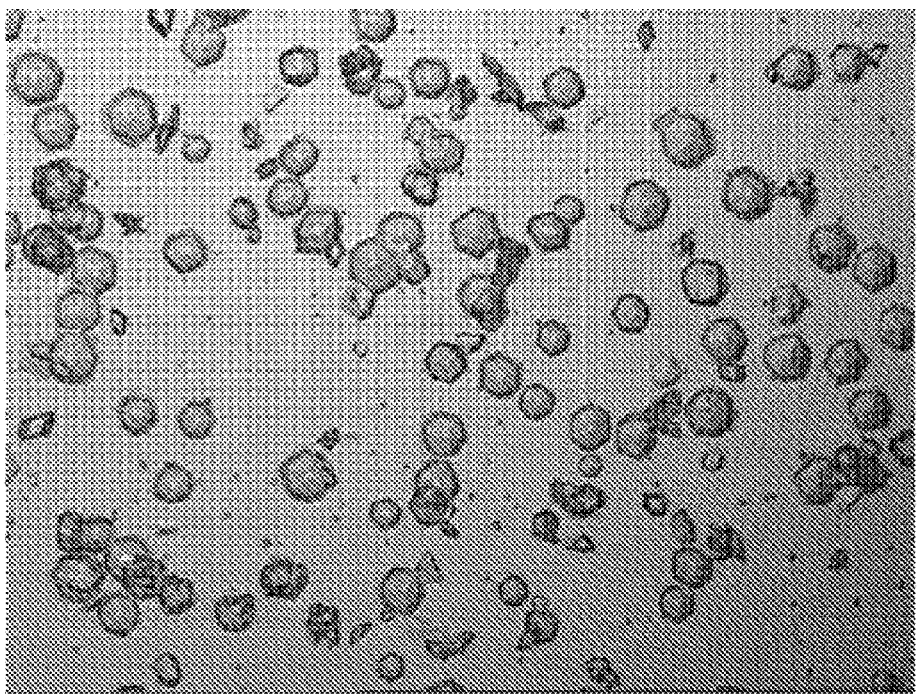
FIG. 2 is a microscopic view photograph at magnification of 160, showing the crystals of recombinant insulin glargine from Example 2.

About 77L of the supernatant is decanted, and the remaining 7L of suspension is respectively added to 1L centrifuge bottle, and centrifuged at 4000 rpm for 10 min. After configuration, the crystal precipitates are removed from all of the centrifuge bottles, and suspended in 0.02M ammonium acetate solution at a concentration of 20 g/L, the suspension is adjusted to pH value of 7.8, washed, centrifuged again to collect the crystal precipitate, washed again, and then centrifuged again for removing the supernatant. After freeze-drying for 40 hours, 245.6 g of freeze dried powder is obtained with water content of 2.3%. Water is added to the freeze-dried powder to form a suspension for microscopic examination, a number of uniform and regular hexahedron crystals can be seen at magnification of 160, and the transparency is high (see: FIG. 2).

EXAMPLE 3

Recombinant insulin glargine crystallization solution is prepared by using the same method as Example 1, in which the components and the concentrations thereof are as follows: recombinant insulin glargine: 2 g/L; n-propanol: 10%; acetic acid: 0.3M; m-cresol: 0.05%; zinc oxide: 20mg/L; sodium acetate: 0.1M.

The initial temperature of the above crystallization solution is adjusted to 4° C., and the pH value thereof is adjusted to pH 7.5-8.5 with ammonium hydroxide, and the solution stands at 4° C. to crystallize for about 10 hours. The supernatant is then taken for HPLC detection, the content of recombinant insulin glargine in the supernatant is 0.05 mg/ml and meets the requirements.

Figure 3:
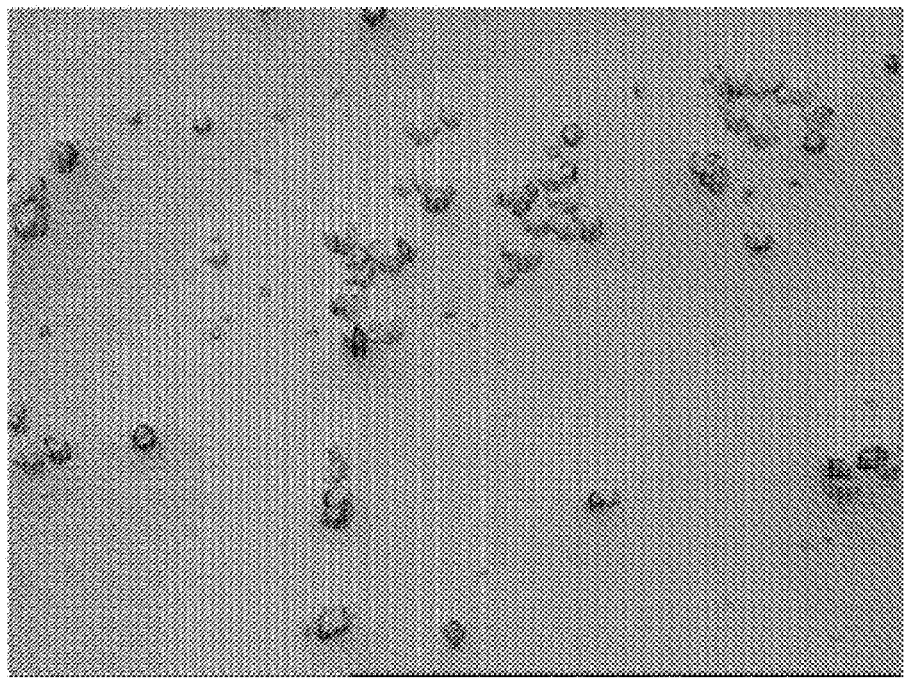
FIG. 3 is a microscopic view photograph at magnification of 160, showing the crystals of recombinant insulin glargine from Example 3.

By microscopic examination after stirring the crystallizing suspension, hexahedron crystals can be seen at magnification of 160, and the transparency is high (see: FIG. 3).

EXAMPLE 4

Recombinant insulin glargine crystallization solution is prepared by using the same method as Example 1, in which the components and the concentrations thereof are as follows: recombinant insulin glargine: 4 g/L; methanol: 30%; citric acid: 0.8M; methyl p-hydroxybenzoate: 0.5%; zinc acetate: 200 mg/L; sodium citrate: 0.5M.

The initial temperature of the above crystallization solution is adjusted to room temperature, and the pH value thereof is adjusted to pH 8.5-9.0 with ammonium hydroxide. The solution is taken out after it stands at 2-8° C. to cool for 1 hour; the pH value thereof is adjusted to pH 7.5-8.0 with glacial acetic acid, and then the solution stands at 2-8° C. for 8 hours. Then the supernatant is taken for HPLC detection, the content of recombinant insulin glargine in the supernatant is as low as 0.04 mg/ml and meets the requirements.

Figure 4:
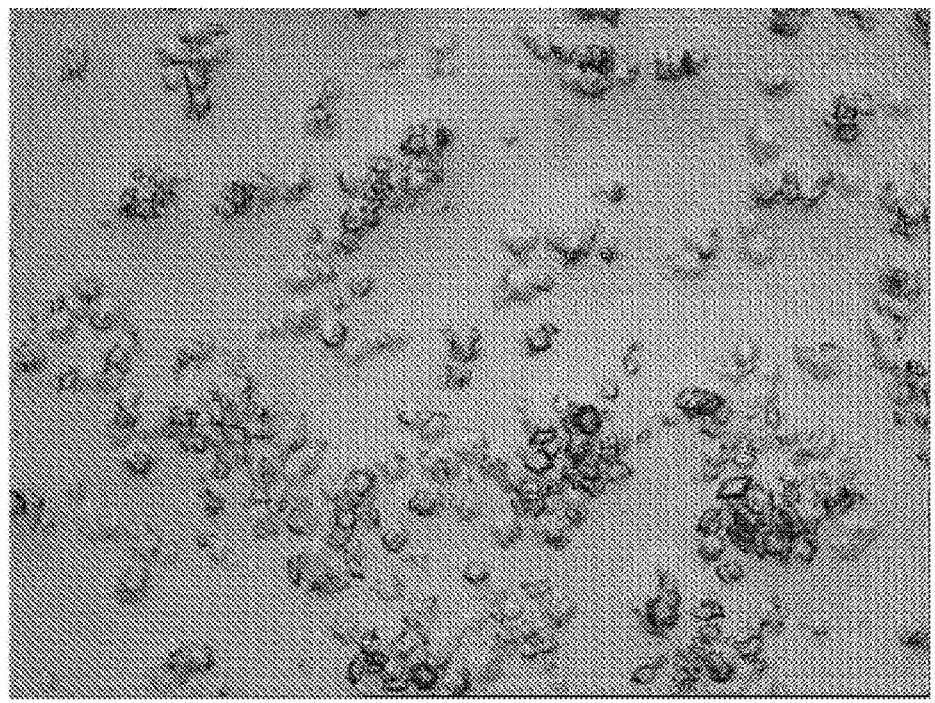
FIG. 4 is a microscopic view photograph at magnification of 160, showing the crystals of recombinant insulin glargine from Example 4.

By microscopic examination after stirring the crystallizing suspension, hexahedron crystals can be seen at magnification of 160, and the transparency is high (see: FIG. 4).

EXAMPLE 5

Recombinant insulin glargine crystallization solution is prepared by using the same method as Example 1, in which the components and the concentrations thereof are as follows: recombinant insulin glargine: 2.8 g/L; isopropanol: 15%; propionic acid: 0.4M; ethyl p-hydroxybenzoate: 0.1%; zinc bromide: 70 mg/L; sodium chloride: 0.3M.

The initial temperature of the above crystallization solution is adjusted to 20-25° C., and the pH value thereof is adjusted to pH 7.1-7.8 with ammonium hydroxide. The solution is stirred for 10 min until the solution is slightly turbid, and stands at 2-8° C. to crystallize for about 6 hours. Then the supernatant is taken for HPLC detection, the content of recombinant insulin glargine in the supernatant is 0.03 mg/ml and meets the requirements.

Figure 5:
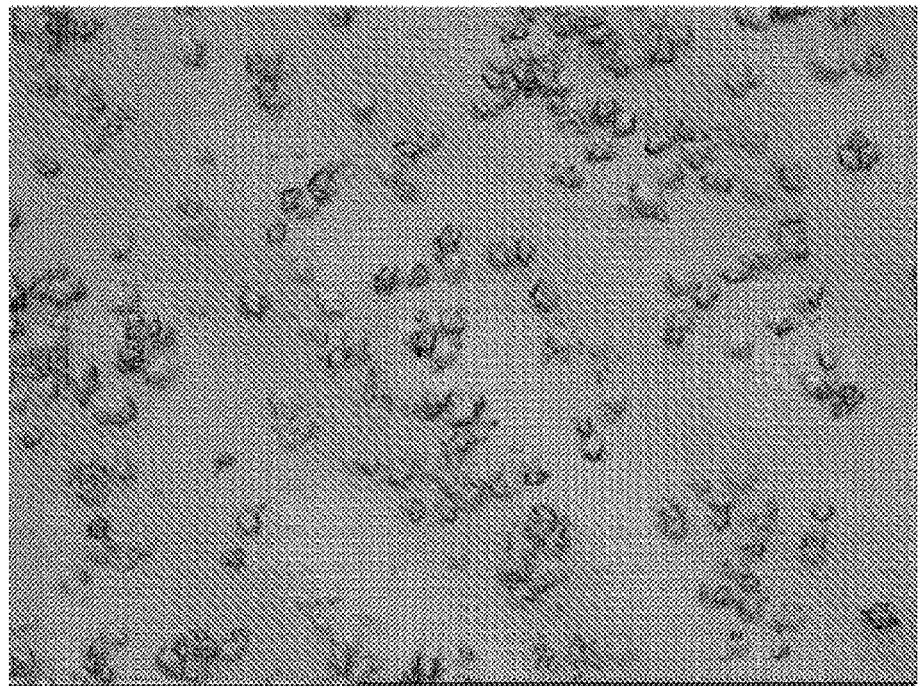
FIG. 5 is a microscopic view photograph at magnification of 160, showing the crystals of recombinant insulin glargine from Example 5.

By microscopic examination after stirring the crystallizing suspension, hexahedron crystals can be obviously seen at magnification of 160, and the transparency is high (see: FIG. 5).

EXAMPLE 6

Recombinant insulin glargine crystallization solution is prepared by using the same method as Example 1, in which the components and the concentrations thereof are as follows: recombinant insulin glargine: 3.2 g/L; t-butanol: 20%; isobutyric acid: 0.6M; phenol: 0.1%; m-cresol: 0.1%; zinc sulfate: 100 mg/L; sodium sulfate: 0.4M.

The initial temperature of the above crystallization solution is adjusted to room temperature, the pH value thereof is adjusted to pH 8.5 with ammonium hydroxide, and then stands at room temperature to crystallize for about 12 hours. The supernatant is taken for HPLC detection, the content of recombinant insulin glargine in the supernatant is 0.05 mg/ml and meets the requirements.

Figure 6:
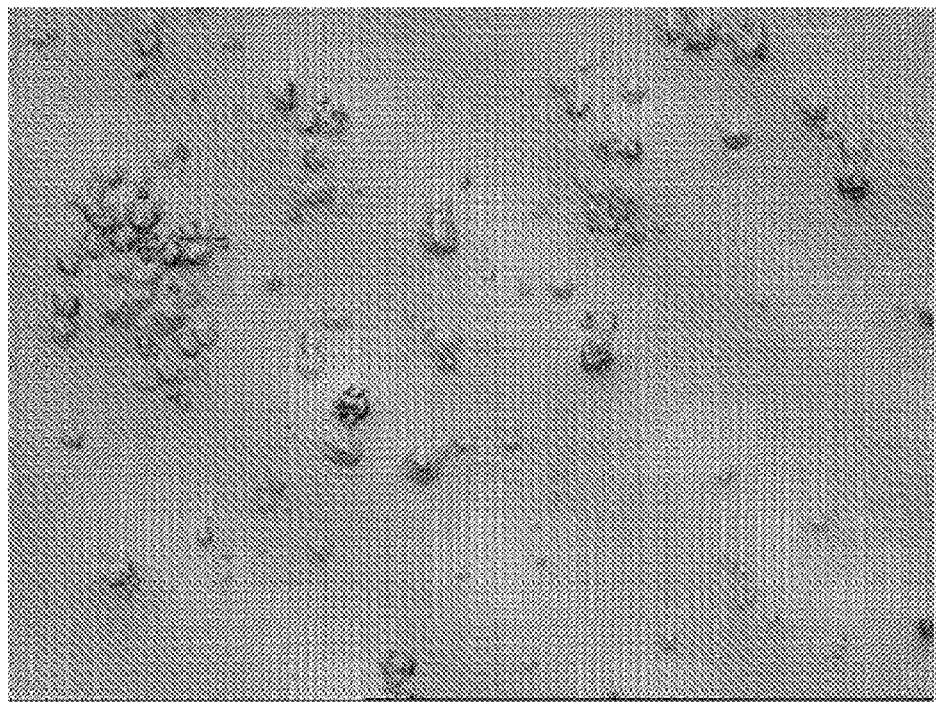
FIG. 6 is a microscopic view photograph at magnification of 160, showing the crystals of recombinant insulin glargine from Example 6.

By microscopic examination after stirring the crystallizing suspension, hexahedron crystals can be obviously seen at magnification of 160, and the transparency is high (see: FIG. 6).

COMPARATIVE EXAMPLE 1

Recombinant insulin glargine crystallization solution is prepared by using the same method as Example 1, in which the components and the concentrations thereof are as follows: recombinant insulin glargine: 1 g/L; ethanol: 5%; acetic acid: 0.1M; zinc chloride: 10 mg/L; phenol: 0.01%; sodium chloride: 0.1M.

The initial temperature of the above crystallization solution is adjusted to 20-25° C., and the pH value thereof is adjusted to pH 8.1-8.8 with ammonium hydroxide. The solution is taken out after standing at 2-8° C. to cool for 1 hour, the pH value thereof is adjusted to pH 7.1-7.8 with glacial acetic acid, and stands at 2-8° C. for 5 hours. Then the supernatant is taken for HPLC detection, the content of recombinant insulin glargine in the supernatant is 0.2 mg/ml.

Figure 7:
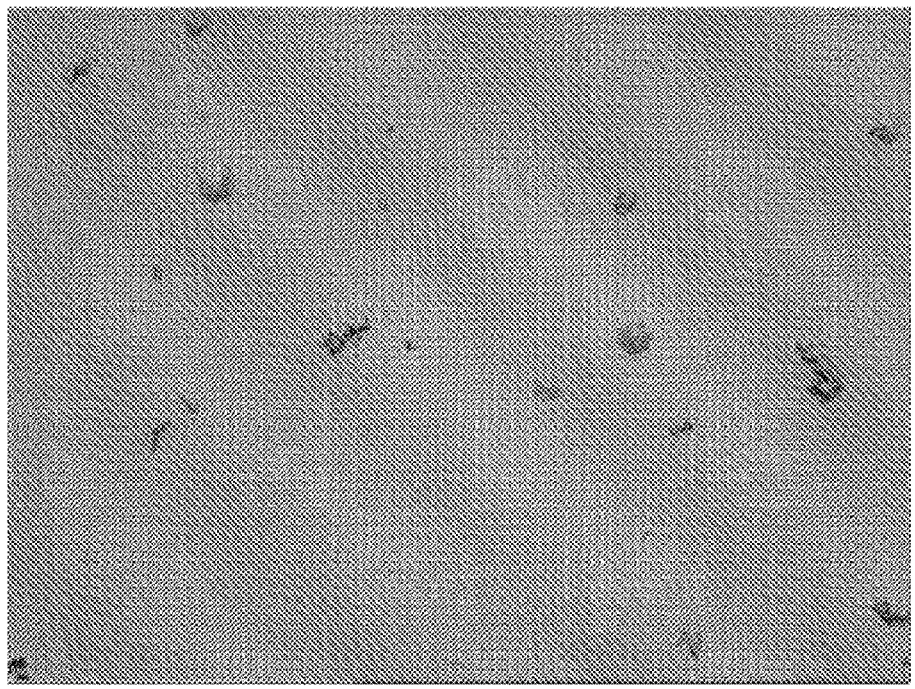
FIG. 7 is a microscopic view photograph at magnification of 160, showing the crystals of recombinant insulin glargine from Comparative Example 1.

By microscopic examination after stirring the crystallizing suspension, few hexahedron crystals can be seen at magnification of 160, and the structures of the crystals are not uniform (see: FIG. 7).

COMPARATIVE EXAMPLE 2

Recombinant insulin glargine crystallization solution is prepared by using the same method as Example 1, in which the components and the concentrations thereof are as follows: recombinant insulin glargine: 30 g/L; ethanol: 50%; acetic acid: 3M; zinc chloride: 300 mg/L; phenol: 2%; sodium chloride: 1M.

The initial temperature of the above crystallization solution is adjusted to 20-25° C., and the pH value thereof is adjusted to pH 8.1-8.8 with ammonium hydroxide. The solution is taken out after standing at 2-8° C. to cool for 1 hour; and the pH value is adjusted to pH 7.1-7.8 with glacial acetic acid, and then stands at 2-8° C. for 5 hours. The supernatant is taken for HPLC detection, the content of recombinant insulin glargine in the supernatant is 0.2 mg/ml.

Figure 8:
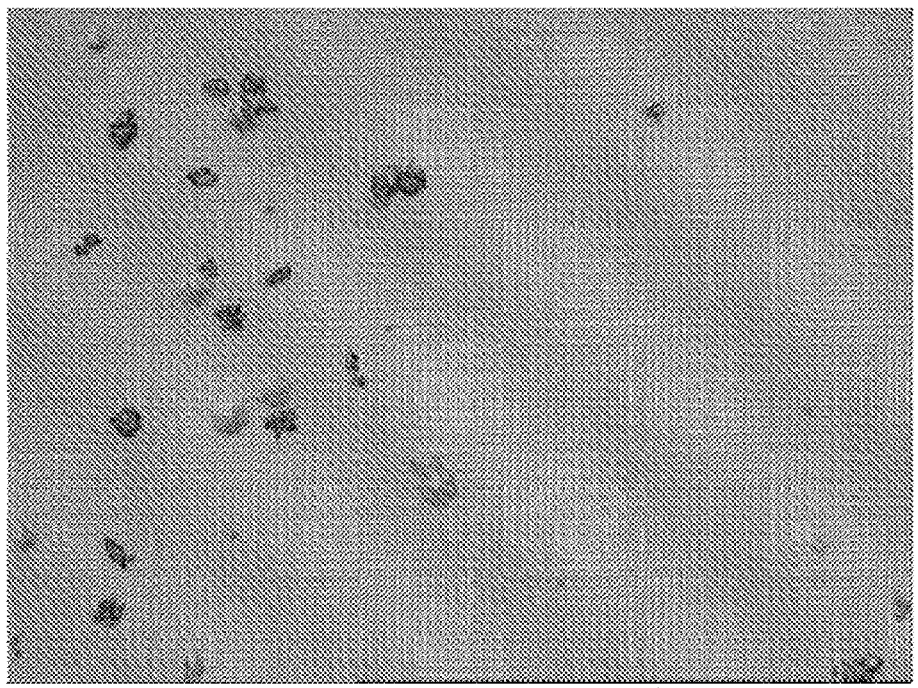
FIG. 8 is a microscopic view photograph at magnification of 160, showing the crystals of recombinant insulin glargine from Comparative Example 2.

By microscopic examination after stirring the crystallizing suspension, few hexahedron crystals can be seen at magnification of 160, and the structures of the crystals are not uniform (see: FIG. 8).

COMPARATIVE EXAMPLE 3

Figure 9:
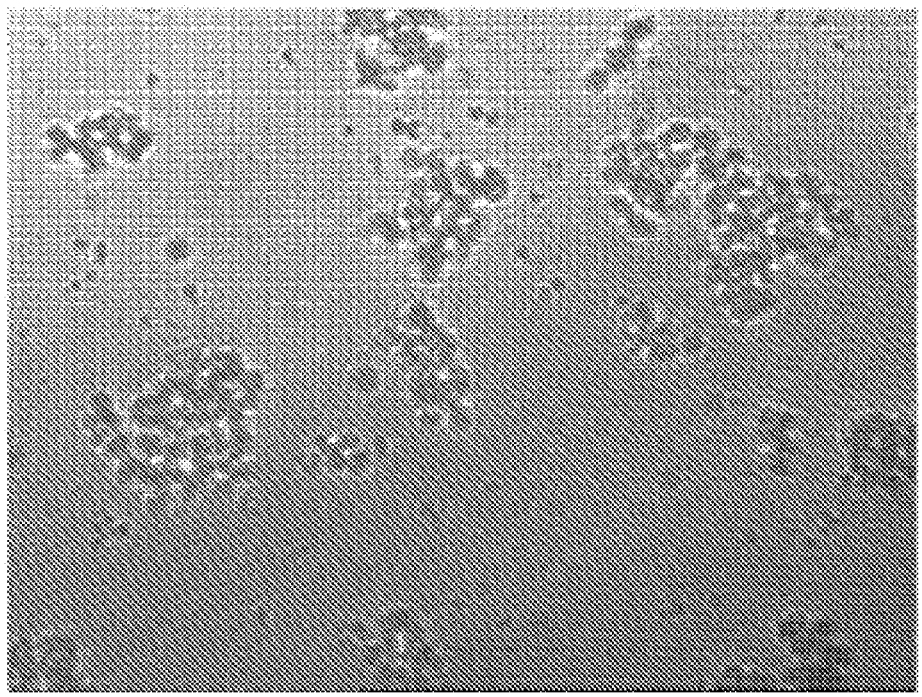
FIG. 9 is a microscopic view photograph at magnification of 160, showing the first part crystals of recombinant insulin glargine from Comparative Example 3.
Figure 10:
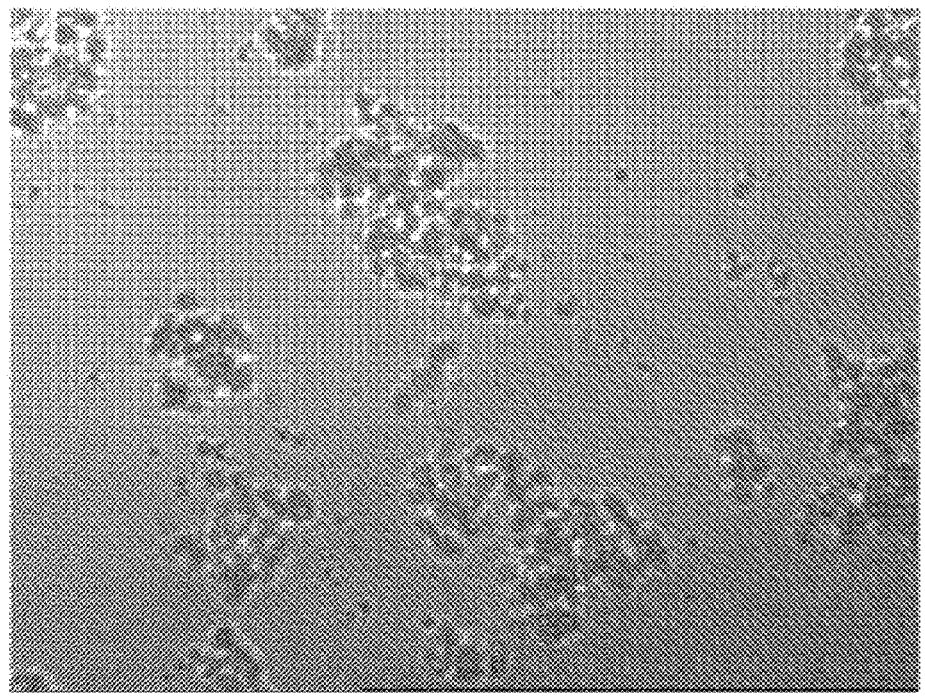
FIG. 10 is a microscopic view photograph at magnification of 160, showing the second part crystals of recombinant insulin glargine from Comparative Example 3.
Figure 11:
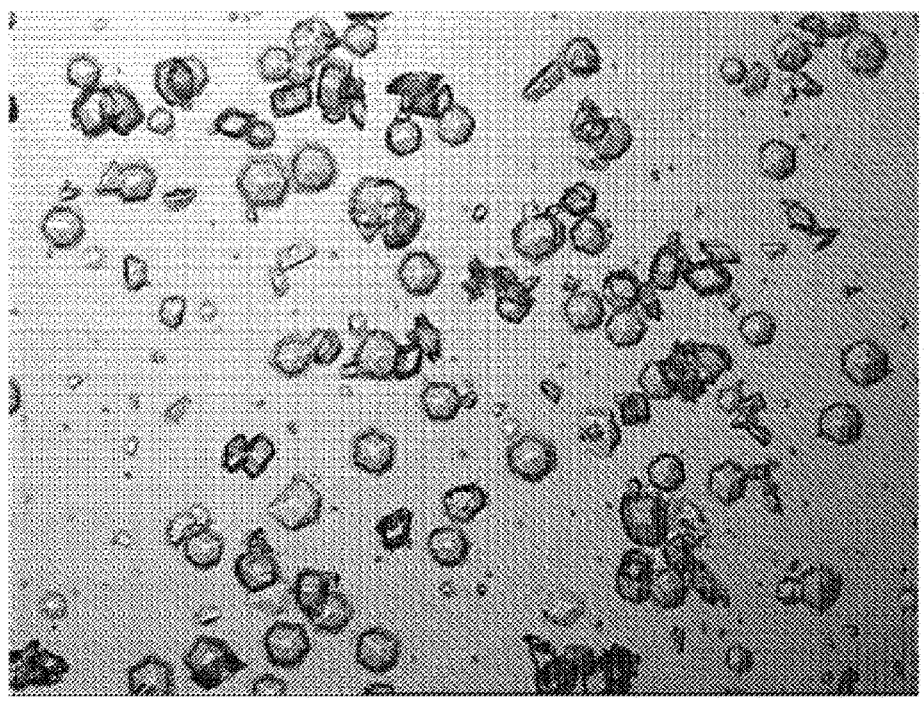
FIG. 11 is a microscopic view photograph at magnification of 160, showing the third part crystals of recombinant insulin glargine from Comparative Example 3.

9 g of recombinant insulin glargine is dissolved in 1.8L of pure water to form a recombinant insulin glargine solution. The solution is divided into three equal parts, then insulin glargine crystals are prepared respectively according to the methods for preparing human insulin, insulin Lyspro and insulin glargine; i.e. (1) glacial acetic acid, zinc chloride and water are added to the first part of the solution, so that the concentration of acetic acid is 0.25M, the concentration of insulin glargine is 1.6-2.1 g/L, the content of zinc reaches 63.5 mg/L, then the pH value of the solution is adjusted to 5.95-6.05 with 4M ammonium hydroxide; (2) glacial acetic acid, zinc chloride, phenol and water are added to the second part of the solution, so that the concentration of acetic acid is 1M, the concentration of insulin glargine is 1.8-2.5 g/L, the content of zinc is 200 mg/L, the content of phenol is 0.2%, then the pH value of the solution is adjusted to 5.9-6.2 with strong ammonium hydroxide; (3) the third part of the solution is formulated according to the components and contents in Example 2. As a result, the first and second parts of the insulin glargine solutions only form flocculent precipitates instead of forming regular hexahedron crystal (see: FIG. 9, FIG. 10), and the third part of the insulin glargine solution forms regular hexahedron crystal (see: FIG. 11).

What is claimed is:

1. A method for preparing a recombinant insulin glargine crystal, comprising the steps of:
   crystallizing the recombinant insulin glargine in a crystallization solution containing a recombinant insulin glargine, an organic solvent, a zinc compound, a phenol derivative, a salt and an organic acid, wherein the concentration of volume percent of the organic solvent is 10-30%, and having an initial pH of 8.0 to 9.0;
   and during the crystallization process adjusting the pH of the crystallizartion soulution to 7.0-8.0.

2. The method according to claim 1, wherein the organic solvent is selected from acetonitrile, ethanol, n-propanol and isopropanol.

3. The method according to claim 1, wherein the initial pH of the crystallization solution is 8.0-8.5, and during the crystallization process the pH of the crystallization solution is adjusted 7.1-7.8.

4. The method according to claim 1, wherein the temperature of crystallization is 1-30° C.

5. The method according to claim 4, wherein the initial temperature of the crystallization solution is 10-30° C., and during the crystallization process the temperature of the crystallization solution is adjusted to 2-8° C.

6. The method according to claim 1, wherein the concentration of the recombinant insulin glargine in the crystallization solution is 2-4 g/L.

7. The method according to claim 1, wherein the phenol derivative is selected from phenol, m-cresol and methyl p-hydroxybenzoate or is a mixture thereof, and the concentration of phenol derivative in the crystallization solution is 0.05-0.5 g/100 ml.

8. The method according to claim 1, wherein the zinc compound is selected from zinc chloride, zinc oxide, zinc acetate, zinc bromide and zinc sulfate, and the concentration of the zinc compound in the crystallization solution is 20-200 mg/L.

9. The method according to claim 1, wherein the salt is selected from sodium chloride, sodium acetate and sodium citrate, and the concentration of the salt in the crystallization solution is 0.1-0.5M.

10. The method according to claim 1, wherein the organic acid is selected from acetic acid, citric acid and glycine, and the concentration of the organic acid in the crystallization solution is 0.3-0.8M.

11. The method according to claim 1, comprising the steps of:
   1) preparing a crystallization solution containing 2.8-3.2 g/L of recombinant insulin glargine, ethanol, 0.1-0.2 g/100 ml of phenol, 0.4-0.6M of acetic acid, 70-100 mg/L of zinc chloride, 0.3-0.4M of sodium chloride under room temperature, wherein the concentration of volume percent of ethanol is 10-30%;
   2) adjusting the pH value of the crystallization solution to 8.0-8.5; and
   3) cooling the crystallization solution to a temperature of 2-8° C., adjusting the pH value to 7.1-7.8, and then crystallizing for at least 3 hours, and thereby obtaining the recombinant insulin glargine crystal.

12. The method according to claim 1, further comprising the steps of: suspending the recombinant insulin glargine crystal at a concentration of 20 g/L in 0.02M of ammonium acetate solution, adjusting the pH value to 7.8, and collecting the precipitate by centrifugation, thereby obtaining the purified recombinant insulin glargine crystal.

13. The method according to claim 12, comprising the following steps of:
   weighing 251.8 g of recombinant insulin glargine, adding thereto 13.1 L of 96% ethanol, 2.4 L of pure glacial acetic acid, 148.6 ml of zinc chloride solution at a concentration of 5.08 g/100 ml, 1678 ml of phenol solution at a concentration of 10%, 1472 g of sodium chloride, and then adding water to a final volume of 83.9 L;
   adjusting the temperature of the above solution to 23±2° C., adjusting the pH value to 8.0-8.5 with strong ammonia, stirring for about 10 min until the solution is slightly turbid, then standing at 2-8° C. for 1 hour and taking it out after cooling, adjusting the pH value to 7.1-7.6 with glacial acetic acid, stirring for about 10 min, and then standing at 2-8° C. for 10 hours;
   decanting about 77 L of the supernatant, adding the remaining 7 L of suspension to 1 L centrifuge bottle respectively, centrifuging at 4000 rpm for 10 min with a centrifuge, taking the crystal precipitates out of all of the centrifuge bottles, suspending the precipitates in 0.02M of ammonium acetate solution at a concentration of 20 g/L, adjusting the pH value to 7.8, washing, collecting the crystal precipitate by a further centrifugation, washing again, then centrifuging again and removing the supernatant, and freeze-drying for 40 hours.

* * * * *